United States Patent [19]

Armand et al.

[11] Patent Number: 5,446,134
[45] Date of Patent: Aug. 29, 1995

[54] BIS(PERFLUOROSULFONYL)METHANE SALTS, AND A PROCESS FOR PREPARING SAME

[75] Inventors: Michel Armand, Saint-Martin-D'Uriage; Djamila Benrabah, Grenoble; Jean-Yves Sanchez, Saint-Ismier, all of France

[73] Assignees: Centre National de la Recherche Scientifique, Paris, France; Hydro Quebec, Montreal, Canada

[21] Appl. No.: 84,217

[22] Filed: Jul. 8, 1993

[30] Foreign Application Priority Data

Nov. 8, 1991 [FR] France ................... 91 13789

[51] Int. Cl.⁶ .................. C07C 317/24; C07C 317/44; C07C 317/04; C07D 317/34; C07D 207/33; C07D 311/66

[52] U.S. Cl. .................... 534/558; 534/565; 534/728; 534/886; 558/397; 558/438; 568/28; 568/31; 568/35; 568/36; 546/340; 546/346; 549/406; 549/394; 548/262.4; 564/440

[58] Field of Search .............. 534/558, 565, 728, 886; 568/28, 31, 35, 36; 558/438, 397; 546/340, 346; 549/394, 406; 564/440; 548/262.4

[56] References Cited

U.S. PATENT DOCUMENTS

| | | | |
|---|---|---|---|
| 3,758,591 | 9/1973 | Koshar | 568/35 X |
| 3,758,593 | 9/1973 | Koshar | 568/35 |
| 3,776,960 | 12/1973 | Koshar | 568/35 |
| 3,794,687 | 2/1974 | Koshar | 568/35 |
| 3,932,526 | 1/1976 | Koshar | 568/35 |
| 5,021,308 | 6/1991 | Armand et al. | 429/194 |
| 5,072,040 | 12/1991 | Armand et al. | 564/82 |
| 5,136,097 | 8/1992 | Armand et al. | 568/28 |
| 5,162,177 | 11/1992 | Armand et al. | 429/194 |

FOREIGN PATENT DOCUMENTS

| | | | |
|---|---|---|---|
| 0267107 | 5/1988 | European Pat. Off. | 568/35 |
| WO92/02966 | 2/1992 | WIPO | 568/35 |

OTHER PUBLICATIONS

Journal of Organic Chemistry, vol. 38, No. 19, Sep. 21, 1973, pp. 3358–3363, R. J. Koshar, et al., "Bis(Perfluoroalkylsulfonyl) Methanes and Related Disulfones".

Chemical Abstracts, vol. 109, No. 1, Jul. 4, 1988, AN 6063p, L. Turowsky, et al., "Tris[(Trifluoromethyl) Sulfonyl] Methane, HC(SO2CF3)", p. 572.

Chemical Abstracts, vol. 114, No. 12, Mar. 25, 1991, AN 105617g, L. A. Dominey, et al., "New Anions For Use In Polymer Electrolyte Rechargeable Lithium Batteries", p. 197.

Primary Examiner—Floyd D. Higel
Attorney, Agent, or Firm—Oblon, Spivak, McClelland, Maier & Neustadt

[57] ABSTRACT

Bis(perfluorosulphonyl)methanes, process for preparing same and uses thereof. The compounds of the invention are based on the formula $(1/nM)+[(R_FSO_2)_2CY]^-$ in which Y denotes an electron-attracting group chosen from $-C\equiv N$ and RZ groupings in which Z denotes a carbonyl grouping, sulphonyl grouping or a phosphonyl grouping and R denotes an organic monovalent grouping, M denotes a metal having valency n or an organic group capable of existing in the cationic form, $R_F$ denotes a perfluoroalkyl or perfluoroaryl grouping. Said compounds are especially useful in the production of electrochemical devices.

22 Claims, No Drawings

BIS(PERFLUOROSULFONYL)METHANE SALTS, AND A PROCESS FOR PREPARING SAME

This application is a 371 of PCT/FR92/01024 filed Nov. 4, 1992.

The present invention relates to bis(perfluorosulfonyl)methane derivatives, to a process for their preparation and to their applications.

Compounds corresponding to the general formula $(R_FSO_2)_2CH_2$ and their salts $1/_nM^{n+}(R_FSO_2)_2CH$, $M^{n+}$ representing a cation of a metal (Li, Na, K, Ca, Cu, La and the like) and an organic cation (ammonium, sulfonium and the like) and $R_F$ representing a perfluoroalkyl ($CF_3$, $C_2F_5$, $C_4F_9$, $C_6F_{13}$ and the like) or perfluoroaryl ($C_6F_5$ and the like) group, are known. These compounds and their process of preparation are described, for example, in U.S. Pat. No. 3,776,960 (Koshar), in R. J. Koshar & R. A. Mitsch, J. Org. Chem., 38, 3358 (1973), or in FR 89.04503 (Armand), These materials have highly acidic properties and their salts are very soluble and dissociate in polar organic solvents or solvating polymers. Nevertheless, the residual hydrogen atom on the carbon has a certain acidity and its reactivity can be a disadvantage in many applications, in particular for the use of these salts in electrochemical cells, and especially those which involve anodes based on metallic lithium, by formation of a dianion:

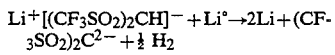

Generally, the lability of this hydrogen can be revealed in a very basic medium (alkoxides, organometallics). According to Koshar, these compounds are prepared by reacting perfluoroalkylsulfonyl halides with a Grignard reagent. According to Armand, the compounds are prepared by reacting an ionic carbide with a sulfonyl halide.

The compounds $(R_FSO_2)_2CHR_H$ and their salts $M(R_FSO_2)_2CR_H$ in which a hydrogen has been replaced by a hydrocarbon radical $R_H$, such as a methyl, allyl or hydroxyethyl, are also known. Thus, Koshar (DE 2,043,381) describes bis(perfluoroalkylsulfonyl)methanes which correspond to the formula $[(R_FSO_2)_2C-R]_yX$, in which R represents a lower alkyl radical and X represents the cation of a nitrogenous base (pyridine, guanidine and the like). Moreover, Koshar (DE 2,419,274) describes bis(perfluoroalkylsulfonyl)methanes which correspond to the formula $[(R_FSO_2)_2C-R]_yX$, in which R represents a lower alkyl radical and X represents a diazonium cation. [R. J. Koshar & R. A. Mitsch J. Org. Chem., 38, 3358 (1973)] describes compounds $M(R_FSO_2)_2CR$ in which R represents a hydrocarbon radical: methyl, allyl or hydroxyethyl, these compounds generally being prepared in low yield from $M(R_FSO_2)_2CH$. In these compounds, the electron-donating nature of the radical $R_H$, reduces the dissociation of the ion pair $M^+[(R_FSO_2)_2CR_H^-]$ and thus the conductivity of the electrolytes obtained by dissolution of these salts in a liquid solvent or polymer. For the same reason, oxidation of the anion is produced at more cathodic potentials, limiting the choice of electrode materials which can be used in electrochemical cells. Compounds $PhN_2^+[C(CF_3SO_2)_3]^-$ (Yagupolskii et al., Chemical Abstracts, Vol. 113, No. 23, 3 Dec. 1992, Columbus, Ohio, U.S.; Abstract No. 211480w) are additionally known. Compounds $K^+[C(CF_3SO_2)_3]^-$ and $Li^+[C(CF_3SO_2)_3]^-$, respectively by L. A. Dominey et al., Chemical Abstracts, Vol. 114, No. 12, 25 March 1991, Columbus, Ohio, U.S.; Abstract No. 105617g) and L. Turowsky et al., Chemical Abstracts, Vol. 109, No. 1, 4 Jul. 1988, Columbus, Ohio, U.S.; Abstract No. 6063p and Inorganic Chemistry, 27, page 2135 (1988), are also known. The compounds are obtained by a high-temperature reaction. The reaction scheme is the following:

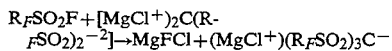

Treatment with sulfuric acid gives the acid. However, the yield of the reaction is low, of the order of 20%.

DE 2,432,414 (Robins) additionally describes bis(perfluoroalkylsulfonyl)methanes which correspond to the formula $(R_FSO_2)_2CHR'$, in which the group $R'$ contains a carbonyl functional group which is not situated directly on the carbon carrying the sulfonyl groups. The group $R'$ thus does not have an electron-withdrawing nature.

Likewise, DE 2,012,011 (Koshar) describes bis-(perfluoroalkylsulfonyl)methanes which correspond to the formula $(R_FSO_2)_2CMCH_2CHBr(CH_2)_mCO_2R'$, in which M represents a metal having a valency from 1 to 4, or a quaternary ammonium. In these compounds, the carbonyl functional group which exists on one of the substituents of the methane, is distant from the carbon carrying the sulfonyl groups. This substituent thus does not have an electron-withdrawing nature. The process for the preparation of these compounds uses an organomagnesium compound.

The aim of the present invention is to provide a process for the preparation of bis(perfluorosulfonyl)methane derivatives containing a strongly electron-withdrawing group on the methine carbanion, the said process making it possible to easily produce derivatives with a good yield.

Another subject of the invention is new bis(perfluorosulfonyl)methane derivatives containing a strongly electron-withdrawing group on the carbon carrying the sulfonyl groups.

Another subject of the invention is various applications of the derivatives.

In accordance with the present invention, the process for the preparation of a compound corresponding to the formula $(1/_nM)+[(R_FSO_2)_2CY]^-$ in which Y represents an electron-withdrawing group chosen from $-C\equiv N$ and the groups RZ— in which Z represents a carbonyl group, a sulfonyl group or a phosphonyl group and R represents a monovalent organic group, M represents a metal having the valency n or an organic group which can exist in the cationic form, and $R_F$ represents a perfluoroalkyl or perfluoroaryl group, is characterized in that it contains a stage in the course of which a compound $(1/_nM')+[(R_FSO_2)_2CH]^-$ is reacted with a compound YX in the presence of an aprotic nucleophilic base Nu, M' representing a metal having the valency n' or a monovalent organic group and X representing a halogen or a pseudohalogen.

The process of the invention consequently makes it possible to convert an anion $(R_FSO_2)_2CH^-$ to an anion $(R_FSO_2)_2CY^-$, Y being a strongly electron-withdrawing group, either $-C\equiv N$ or RZ as defined above. R is a monovalent organic radical which can contain various functionalities suited to the anticipated application of the desired product.

According to a variant, the implementation of the invention comprises the reaction of a halogen with a bis(perfluorosulfonyl)methane derivative. In this case, the halide is preferably chosen from F, Cl and Br.

According to another variant, the implementation of the process of the invention comprises the reaction of a pseudohalide with a bis(perfluorosulfonyl)methane derivative. Pseudohalogen is understood to mean, in the present text, any group other than a halide which can carry a negative charge. By way of example, there may be mentioned the $RS_3$, $RCO_2$, succinimidyloxy (SCO), phthalimidoxy (PTO), 1-benzotriazoloxy (BzO), oxynorbornene-2,3-dicarboximide, trifluoroethoxy, trichloroethoxy, imidazolyl, triazolyl, nitrophenoxy, dinitrophenoxy, perhalophenoxy or o-acylurea radicals.

The aprotic nucleophilic base Nu is preferably chosen from alkylamines, for example triethylamine, diisopropylethylamine or quinuclidine; 1,4-diazabicyclo[2.2.2]octane (TED); pyridines, for example pyridine, alkylpyridines or dialkylaminopyridines; imidazoles, for example N-alkylimidazoles or imidazo[1,2-a]pyridine; amidines, for example 1,5-diazabicyclo[4.3.0]non-5-ene (DBN) or 1,8-diazabicyclo[5.4.0]undec-7-ene (DBU) or guanidines, for example tetramethylguanidine or 1,3,4,6,7,8-hexahydro-1-methyl-2H-pyrimido[1,2-a]pyrimidine (HPP).

In the process of the present invention it is possible to use a nucleophilic base fastened to a macromolecular framework.

The compounds RZX of halide type are advantageously prepared in situ by reacting the corresponding RZOH or RZOM derivatives with a halogenating agent. Among the particularly preferred halogenating agents, there may be mentioned: $SOCl_2$, $SOBr_2$, $SF_4$, $(C_2H_5)_2NSF_3$, $COCl_2$, $(COCl)_2$, $(COBr)_2$, $(CCl_3O)_2CO$, $[(CH_3)_2N=CHCl]^+Cl^-$, triphenylphosphine ($P\phi_3$)/$CCl_4$ mixture, dichloromethyl methyl ether $Cl_2HCOCH_3$, and 2-chloro-1-methylpyridinium or 2-fluoro-1-methylpyridinium salts.

In the specific case where Z=CO, it is particularly advantageous to use a compound RZX of pseudohalide type prepared directly in situ (X=$RCO_2$, SCO, PTO, BzO and the like) from RCOOH by the action of condensation agents used in peptide synthesis (molecular dehydrating agents). Such agents are described, for example, in Synthesis, p. 453 (1972) and in Ann. Rev. Biochem., 39, 841 (1970). The compounds of the invention are then prepared from the RCOOH+($1/_n$M)[(R$_F$SO$_2$)$_2$CH] stoichiometric mixture in a porous solvent to which the molecular dehydrating agent is added. These condensation agents are preferably chosen from carbodiimides, for example cyclohexyldiisopropylcarbodiimide; alkyl ethynyl ethers $R_H$—O—C≡CH; succinimidyl, phthalimidyl, 1-benzotriazolyl, nitrophenyl, dinitrophenyl, perhalophenyl, trifluoroethyl or trichloroethyl carbonates and oxalates; the $P\phi_3$-diethylazodicarboxylate (DEAD) mixture or $P\phi_3$-dithiodipyridine mixture; carbonyldiimidazole (Im)$_2$CO or phenylphosphorodiimidazote $\phi$PO(Im)$_2$; amide acetals, for example dimethylformamide di-neopentyl acetal $(CH_3)_2NCH[OCH_2C(CH_2)_2]_2$; 2-alkoxy-1-alkoxycarbonyl-1,2-dihydroquinoline; O-benzotriazol-1-yl-N,N,N',N'-tetramethyluronium or O-benzotriazol-1-yloxytrisdimethylaminophosphonium salts; aromatic sulfones, for example 6-nitronaphth[1,8-cd][1,2]oxathiole 2,2-dioxide, isobutyl chloroformate, diphenylphosphorochloroiridate, ethylene chlorophosphite, diethylethylene pyrophosphite; bis(2-oxo-3-oxazolidinyl)-phosphinic chloride; 2-(terbutyl)-5-methylisoxazolium salts (Woodward's reagent L).

When the solubility of the compound $(M'1/_n)^+X^-$ in the reaction medium is less than that of the compound (NuH)$^+$[(R$_F$SO$_2$)$_2$CY]$^-$, $(M'1/_n)^+X^-$ precipitates and the reaction medium contains the compound (NuH)$^+$[(R$_F$SO$_2$)$_2$CY]$^-$ in solution. In this case, if the cation (NuH)$^+$ does not correspond to the desired cation $(1/_nM)^+$, the process of the invention includes an additional stage during which the compound (NuH)$^+$[(R$_F$SO$_2$)$_2$CY]$^-$ is reacted with a suitable salt of the cation M in order to carry out cation exchange. This salt can be, for example, a carbonate, a phosphate, an oxide or a hydroxide.

Another solution consists in reacting the compound (NuH)$^+$[(R$_F$SO$_2$)$_2$CY]$^-$ with an anhydrous acid, for example sulfuric acid, to produce the corresponding acid (R$_F$SO$_2$)$_2$CHY which can be separated using a suitable solvent or by distillation; this acid can itself be converted to a salt by addition of a suitable compound such as a carbonate, a phosphate, an oxide or a hydroxide.

The compounds of the present invention correspond to the formula $(1/_nM)^+$[(R$_F$SO$_2$)$_2$C(Y)]$^-$, in which M, R$_F$, Y and n have the meaning given above, $(1/_nM)^+$ being other than Li$^+$, K$^+$ or a diazonium cation when Y represents CF$_3$SO$_2$.

R$_F$ is preferably a $C_1$ to $C_{20}$, preferably $C_1$ to $C_8$, perfluoroalkyl group.

R$_F$ can also be chosen from $C_6$ to $C_{20}$, preferably $C_6$ to $C_7$, perfluoroaryl groups.

M can be a metal, chosen from alkali metals, alkaline-earth metals, transition metals having the valency 1, 2 or 3, zinc, cadmium, mercury or the lanthanides. Specific preferred compounds are those for which M is an alkali metal or Zn or Mg or La.

M can also be NuH, Nu being chosen from ammonia, alkylamines, pyridines, imidazoles, amidines, guanidines, alkaloids or diazonium compounds.

M can additionally be a sulfonium, an oxonium or a phosphonium.

The radical Y, as defined above, has an electron-withdrawing nature, whether it is —C≡N or RZ—.

When Y is of the RZ— type, the bifunctional group —Z— (representing —CO—, —SO$_2$— or —R'PO—) has a sufficiently high electron-withdrawing nature, whatever the organic group R, for the delocalization of the anionic charge on the anion [(R$_F$SO$_2$)$_2$CY]$^-$ to be increased with respect to the delocalization of the anionic charge on the anion [(R$_F$SO$_2$)$_2$CH]$^-$. Thus, the replacement of the hydrogen atom of the sulfonylmethane derivative by a radical Y as defined above improves the dissociation ability of the salt. For this reason, the compounds of the present invention are particularly useful as ionic-conduction materials in electrochemical cells. The compounds of the present invention can constitute the electrolyte or a part of one of the electrodes when a composite electrode is being used.

The group R can be chosen to confer on the compound of the invention an additional property or properties for the purpose of its use. The choice of R is consequently very wide. When R carries groups capable of reacting themselves during the reaction which is carried out during the implementation of the process of the invention, these groups will be protected before the reactant R$_2$X is introduced into the reaction medium. They will be deprotected by a suitable treatment of the compound obtained after the reaction.

Generally, R can be chosen from $C_1$–$C_{30}$ alkyl or $C_1$–$C_8$ perhaloalkyl radicals, $C_6$–$C_{12}$ aryl or perhaloaryl radicals, arylalkyl radicals, oxaalkyl, azaalkyl or thiaalkyl radicals and heterocycles.

More particularly, when R is an alkyl radical, an arylalkyl radical or a perhaloalkyl radical having more than 4 carbon atoms, the compound of the present invention has surface-active properties.

When R represents a mesomorphic group, the compound of the invention has the properties of a liquid crystal.

When R contains ethylenic unsaturations, for example —C=C—, —C=C—C=O, —C=C—$SO_2$— or —C=Cφ, the compound of the invention can be polymerized.

When R contains at least one functional group which can be condensed, such as, for example, —OH, —$NH_2$ or —COOH, —N=C=O, the compound of the invention can be incorporated into a network obtained by polycondensation.

When R contains a group which can be dissociated, such as, for example, a peroxide group —O—O—, a diazo group —N=N, an azo group $N_2$=CH—, an —$SO_2N_3$ group, or a disulfide group —S—S—, the compound of the invention can be used as a radical initiator.

The group R can consist of a polymeric chain carrying grafts containing one or the other of the biradicals —Z—. By way of example, there may be mentioned a poly(acryloyl) or a poly(styrenesulfonyl). The compound of the invention can then constitute a polyelectrolyte.

The group R can be a hindered phenol or a quinone. The compound of the invention then constitutes a free-radical trap and has anti-oxidizing properties.

When R is a chromophoric group, for example Rhodamine B, the compound of the invention is a coloring agent.

When R contains a cyclic ester, nitrile or amide functional group, the compound of the invention constitutes a dissociating dipole.

R can also contain a redox couple such as, for example, a disulfide, a thioamide, a ferrocene, a phenothiazine, a bis(dialkylamino)aryl, a nitroxide or an aromatic imide.

R can also be a doped electrically-conducting polymer.

R can also constitute a complexing ligand or a zwitterion.

R can additionally be an optically or biologically active polypeptide, amino acid or hydrolyzable alkoxysilane.

The present invention is illustrated by the following non-limiting examples:

EXAMPLE 1

This example illustrates the process of the invention in which a bis(fluorosulfonyl)methane salt reacts with a cyanogen halide.

15.9 g of the potassium salt of bis(trifluoromethanesulfonyl)methane in 50 ml of acetonitrile and 10 ml of pyridine are added to 10 ml of a commercial 5M solution of cyanogen bromide in acetonitrile. A precipitate of potassium bromide is formed which is removed by filtration. The resulting colorless solution is evaporated and then taken up in 70 ml of acetone and stirred with 8 g of $K_2CO_3$. The suspension is filtered and evaporated to give 14.5 g of the salt $K^+[(CF_3SO_2)_2CC\equiv N]^-$.

Examples 2 to 8 illustrate the process of the invention in which a bis(fluorosulfonyl)methane salt reacts with a halide RZX prepared beforehand.

EXAMPLE 2

3.02 g of the sodium salt of bis(trifluoromethanesulfonyl)methane are dissolved in 10 ml of acetonitrile and 1 ml of pyridine is added. The mixture is cooled to $-20°$ C. and condensation is carried out with 1.33 g of trifluoroacetyl chloride. The reaction is written as:

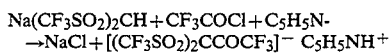

$Na(CF_3SO_2)_2CH + CF_3COCl + C_5H_5N \rightarrow NaCl + [(CF_3SO_2)_2CCOCF_3]^- \, C_5H_5NH^+$ The sodium chloride precipitate is removed by filtration and the solvent evaporated at 40° C. in a rotary evaporator. After addition of 10 ml of acetone, the solution is stirred for 24 hours with 1.5 g of lithium phosphate $Li_3PO_4$. After evaporation, a white solid is obtained which analyses as: C=13% (12.9); F=45% (46.2); S=22% (23.7); Li=1.9% (1.9) with a yield of 91%. The theoretical data for $Li(CF_3SO_2)_2CCOCF_3$ are given in brackets.

EXAMPLE 3

3.02 g of the sodium salt of bis(trifluoromethanesulfonyl)methane are dissolved in 15 ml of acetonitrile, and 150 μl of triethylamine and 50 mg of dimethylaminopyridine are added. The mixture is cooled to $-20°$ C. and condensation is carried out in the reactor with 1.52 g of trifluoromethanesulfonyl fluoride. The temperature is brought slowly to room temperature so that the pressure in the reactor does not exceed 1.5 atmospheres. The reaction is written as:

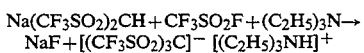

$Na(CF_3SO_2)_2CH + CF_3SO_2F + (C_2H_5)_3N \rightarrow NaF + [(CF_3SO_2)_3C]^- \, [(C_2H_5)_3NH]^+$ The dimethylaminopyridine acts as a catalyst for the transfer of the trifluoromethylsulfonyl group. The sodium fluoride precipitate is removed by filtration and the solvent is evaporated at 40° C. in a rotary evaporator. After addition of 10 ml of acetone, the solution is stirred for 24 hours with 2.4 g of anhydrous potassium phosphate $K_3PO_4$. After evaporation, a white solid is obtained which analyses as: C=11% (theoretical for $K(CF_3SO_2)_3C$: 10.6); F=37% (38); S=20.5% (21.3); K=8.5% (8.6) with a yield of 88%.

EXAMPLE 4

3.3 g of stearic acid chloride $C_{17}H_{35}COCl$ in 25 ml of THF and 5 ml of anhydrous pyridine are added to 3.02 g of the sodium salt of bis(trifluoromethanesulfonyl)methane in 25 ml of THF. The solution is filtered to remove the sodium chloride precipitate and is then brought into contact with 500 mg of lithium carbonate $Li_2CO_3$. The mixture is stirred for 24 hours; the excess carbonate is removed by centrifuging and the solvent is evaporated. There are obtained 4.8 g of the salt $[C_{17}H_{35}CO(CF_3SO_2)_2C]^-Li^+$ which has marked surface-active properties, including in aprotic solvating polymers and solvents.

EXAMPLE 5

A 10% solution of poly(acryloyl chloride) in dioxane is obtained by radical polymerization of the corresponding monomer. 9.05 g of this solution are added to 3.02 g of the sodium salt of bis(trifluoromethanesulfonyl)methane dissolved in 5 ml of pyridine and 5 ml of acetonitrile. The sodium chloride precipitate is removed by centrifuging and the supernatant solution is treated with 1.5 g of lithium carbonate with magnetic stirring for 48 h. After filtration, there is obtained the lithium salt of a polyelectrolyte which is soluble in polar aprotic solvents, such as DMF, acetonitrile and the like, unlike other polymers carrying ionophoric groups of carboxylate or sulfonate type. 341 mg of this polymer and 900 mg of polyethylene glycol 400-cooxymethylene with a mass $M_w \simeq 10^5$ daltons, prepared according to the method described in: C. V. Nicholas, D. J. Wilson, C. Booth and R. J. M. Giles, Brit. Polym. J., 20, 289 (1988), are dissolved in 15 ml of acetonitrile. After spreading the resulting solution and evaporation of the solvent, there is obtained a film of an elastomer formed from the mixture of the solvating polymer and of the polyelectrolyte. This material has a conductivity due solely to the $Li^+$ cation of $1 \times 10^{-5}$ $(\Omega \cdot cm)^{-1}$ at 25° C.

EXAMPLE 6

324 mg of 4-(dimethylamino)azobenzene-4'-sulfonyl chloride in 5 ml of THF are added to 602 mg of the sodium salt of bis(nonafluorobutanesulfonyl)methane in 5 ml of THF and 500 μl of triethylamine. The sodium chloride precipitate is removed and, by evaporation, there is obtained the triethylammonium salt which is suspended in 5 ml of water containing 350 mg of tetrabutylammonium bromide in solution. The mixture is stirred for 24 h. There is obtained an orange-colored powder which is soluble in the majority of organic solvents and which corresponds to the following formula:

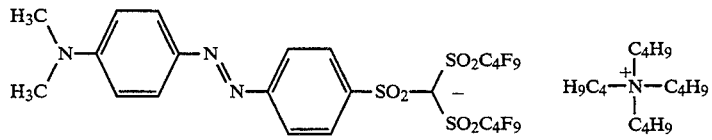

This ionic coloring agent is a pH indicator in nonaqueous medium(yellow-orange/red-violet transition in the pH-1-4 region).

EXAMPLE 7

10.8 g of methoxyacetic acid chloride are diluted in 150 ml of acetonitrile and 15 ml of anhydrous pyridine. The mixture is maintained under a nitrogen atmosphere and magnetic stirring, and 31.8 g of the potassium salt of bis(trifluoromethanesulfonyl)methane are added in portions. When potassium chloride precipitation has finished (several minutes), 25 g of anhydrous tripotassium phosphate $K_3PO_4$ are added and the mixture is stirred for 24 hours. The mixture is then evaporated to dryness. The salt obtained, $K[CH_3OCH_2COC(SO_2CF_3)_2]$ is purified by recrystallization from a butanone/1,2-dichloroethane mixture.

EXAMPLE 8

3.02 g of the sodium salt of bis(trifluoromethanesulfonyl)methane are dissolved in 15 ml of acetonitrile and 5 ml of anhydrous pyridine. 1.48 ml of bis(dimethylamino)phosphorochloridate are added. The mixture is stirred for 2 h at ordinary temperature. The sodium chloride precipitate is removed by filtration and the solvent is evaporated at 40° C. in a rotary evaporator. After addition of 10 ml of acetone, the solution is stirred for 24 hours with 2.4 g of anhydrous potassium phosphate $K_3PO_4$. Evaporation of the acetone provides the salt, $K^+\{[(CH_3)_2N]\}_2PO(CF_3SO_2)_2C^-\}$, in the form of colorless microcrystals.

Examples 9 to 12 illustrate the process of the invention in which a bis(fluorosulfonyl)methane salt reacts with a halide prepared in situ.

EXAMPLE 9

18.8 g of potassium trifluoromethanesulfonate are dissolved in 150 ml of acetonitrile and the solution is cooled to 0° C. 12.8 g of (chloromethylene)dimethylammonium chloride $[(CH_3)_2N=CHCl]^+Cl^-$ are added and a potassium chloride precipitate is formed. 31.8 g of the potassium salt of bis(trifluoromethanesulfonyl)methane and 8.5 ml of N-methylimidazole are added. The mixture is stirred at 0° C. for 1 h and then for 4 h at ordinary temperature. After filtration, the solvent is evaporated and the solid residue is dissolved in 100 ml of water to which 20 g of cesium chloride have been added. The precipitate formed, $Cs(CF_3SO_2)_3C$, is separated and dried. The acid, $H(CF_3SO_2)_3C$, is obtained by distilling the cesium salt with an excess of anhydrous sulfuric acid under reduced pressure. Treatment of the acid $H(CF_3SO_2)_3C$ with the hydroxides or carbonates of M makes it possible to prepare the salts $M(CF_3SO_2)_3C$.

EXAMPLE 10

A sulfonated oligomer of poly(ethylene oxide), POE, is prepared by a procedure similar to that described by T. Hamaide, C. Carré & A. Guyot (Proceedings of the Second International Symposium on Polymer Electrolytes, B. Scrosati ed., Elsevier Applied Science, London, 1990, page 175): 10 g of POE with a mass of 600 are dried by azeotropic distillation with benzene and freeze drying. After addition of 50 ml of THF, the end OH groups are metallated with potassium/naphthalene. The stoichiometry is determined by colorimetry, the end of the reaction being shown by the persistence of the intense green color of the naphthalene radical anion. 4.10 g of propanesultone are then added. After evaporation of the solvent, the α,ω-disulfonated polymer is obtained in the powder form and the residual naphthalene is removed by washing with hexane. 5 g of the product thus formed, suspended in 15 ml of acetonitrile, are treated with 1.8 g of (chloromethylene)dimethylammonium chloride $[(CH_3)_2N=CHCl]^{+Cl-}$. A potassium chloride precipitate is formed after approximately 1 h. 4.4 g of the potassium salt of bis(trifluoromethanesulfonyl)methane and 3 ml of anhydrous pyridine are added to this suspension. After filtration, the reaction mixture is stirred in the presence of 2 g of lithium phosphate $Li_3PO_4$. A second filtration makes possible the separation of a colorless solution which, by concentration, gives a viscous fluid. This material makes it possible to plasticize a large number of polymers containing polar units (ether, amide, nitrile, ester and the like) while conferring on them a high ionic conductivity.

EXAMPLE 11

A non-ionic surface-active agent of Brij ® 35 type, polyoxyethylene (23) lauryl ether $C_{12}H_{25}(OCH_2CH_2)_{23}OH$, is sulfonated by a procedure similar to that described in Example 10: 12 g of Brij 35 ® are dried by azeotropic distillation with benzene and freeze drying. After addition of 50 ml of THF, the end OH groups are metallated with sodium hydride in the presence of 5 mg of triphenylmethane. The stoichiometry is determined by colorimetry, the end of the reaction being indicated by the persistence of the intense red color of the $\phi_3 C^-$ anion. 1.4 g of 1,4-butanesultone are then added. After evaporation of the solvent, the sulfonated oligomer is obtained in the powder form. 5 g of the product thus formed in suspension in 15 ml of acetonitrile are treated with 1 ml of thionyl chloride and 20 μl of dimethylformamide. A sodium chloride precipitate is formed over 20 min. After filtration, the solvent and the excess $SOCl_2$ are evaporated under reduced pressure. The residue is dissolved in 30 ml of pyridine and added to 1.2 g of the sodium salt of bis(trifluoromethanesulfonyl)methane. After filtration, the reaction mixture is stirred in the presence of 1 g of lithium phosphate $Li_3PO_4$. A second filtration makes possible the separation of a colorless solution which, by concentration, gives a wax. This material has surface-active and plasticizing properties.

EXAMPLE 12

380 mg of ethylenebis(oxyethylenenitrilo)tetraacetic acid in 10 ml of pyridine are treated with 350 μl of thionyl chloride at ordinary temperature for 24 h. The excess $SOCl_2$ and pyridine are evaporated and 1.208 g of the sodium salt of bis(trifluoromethanesulfonyl)methane in 15 ml of a mixture of equal volumes of pyridine and acetonitrile are added. The NaCl precipitate is removed and the solution is stirred with 1 g of anhydrous potassium carbonate $K_2CO_3$. After filtration, the solution is evaporated and provides colorless crystals of:

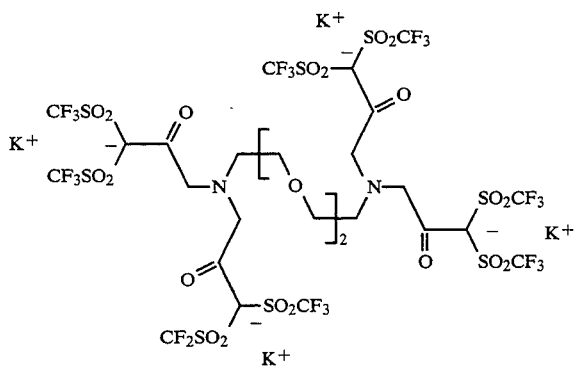

This compound is a ligand (L) of divalent ($A^{II}$) and trivalent ($A^{III}$) metals. The corresponding complexes $[A^{II}L]^{2-}M^+$ and $[A^{III}L]^{-2}M^+$ are soluble salts in polar aprotic media and in polar polymers, in particular polyethers. These complexes in which the central metal A is protected from external electrostatic influences are advantageous for building lasers. Furthermore, they make possible redox reactions by changing the oxidation state of the metal A.

Examples 13 to 23 illustrate the process of the invention in which a bis(fluorosulfonyl)methane salt reacts with a pseudohalogen prepared in situ.

EXAMPLE 13

400 mg of lauric acid $C_{11}H_{23}COOH$ in 5 ml of THF and 1 ml of anhydrous pyridine are added to 636 mg of the potassium salt of bis(trifluoromethanesulfonyl)methane and 500 mg of 2-ethoxy-1-ethoxycarbonyl-1,2-dihydroquinoline (EEDQ). The mixture is stirred for 48 hours and the solvent is evaporated. The residue is treated under primary vacuum at 110° C. for 20 hours. The salt $[C_{11}H_{23}CO(CF_3SO_2)_2C]^- K^+$ is obtained, which salt has marked surface-active properties, including in aprotic solvating polymers and solvents.

EXAMPLE 14

548 mg of 1,1'-ferrocenedicarboxylic acid and 1 14 g of the lithium salt of bis(trifluoromethanesulfonyl)methane are dissolved in 5 ml of pyridine. 824 mg of dicyclohexylcarbodiimide are added. The mixture is maintained under magnetic stirring at room temperature for 75 h. The cyclohexylurea precipitate is removed by centrifuging and the solution is evaporated. There is obtained a hygroscopic dark-brown solid of $[Li(CF_3SO_2)_2CCOCH_5H_4]_2Fe$ which is soluble in the majority of the complexing polar solvents.

EXAMPLE 15

324 mg of 6-hydroxy-2,5,7,8-tetramethylchroman-2-carboxylic acid (Trolox ®):

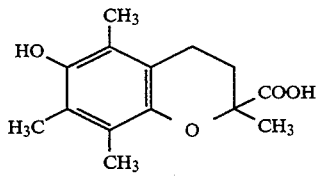

are suspended in 10 ml of ethyl acetate and 1 ml of pyridine. 836 mg of the potassium salt of bis(pentafluoroethanesulfonyl)methane and 313 μl of 1,3-diisopropylcarbodiimide are added to this mixture. After 24 h, the diisopropylurea precipitate is filtered and the volume of the solution is reduced to 2 ml using a rotary evaporator. 20 ml of hexane are added and the mixture is cooled to −10° C. The white precipitate is collected by filtration. The analysis corresponds to $C_{19}H_{17}F_{10}KO_7S_2$. This product has anti-oxidizing properties, in particular for polymers. The same is true of the derivatives of other cations, including organic cations such as tetraalkylammonium cations.

EXAMPLE 16

2.8 g of 4,4'-azobis(4-cyanovaleric) acid are suspended in 20 ml of methyl formate and 5 ml of pyridine. 5.72 g of the lithium salt of bis(trifluoromethanesulfonyl)methane and 4.16 g of dicyclohexylcarbodiimide are added. The mixture is maintained under magnetic stirring at 0° C. for 48 h. The dicyclohexylurea precipitate is removed by centrifuging and the solution is evaporated at ordinary temperature. There is obtained a white crystalline solid of:

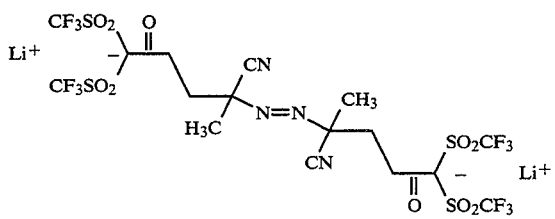

[Li(CF₃SO₂)₂CCOCH₂CH₂(CN)(CH₃)CN≡]₂ which is soluble in particular in ether, acetone, acetonitrile or ethyl acetate. This salt can be used as a radical initiator for initiating polymerization or crosslinking reactions from 60° C.

EXAMPLE 17

858 mg of the lithium salt of bis(trifluoromethanesulfonyl)methane, 618 mg of dicyclohexylcarbodiimide and 10 mg of 1,8-diazabicyclo[5.4.0]undec-7-ene (DBU) are added to 258 mg of vinylacetic acid in 10 ml of 1,2-dimethoxyethane (glyme). The mixture is maintained under magnetic stirring at 0° C. for 48 h. The dicyclohexylurea precipitate is removed by centrifuging and the salt obtained by evaporation of the solvent under reduced pressure.

EXAMPLE 18

76 g of carboxypropyl disulfide [—S(CH₂)₃COOH]₂ are dissolved in 100 ml of pyridine with 12.08 g of the sodium salt of bis(trifluoromethanesulfonyl)methane and 8.24 g of dicyclohexylcarbodiimide. After stirring for 48 h, the mixture is filtered and evaporated. The residual solid is dissolved in 50 ml of water and 12 g of tetrapropylammonium bromide are added. The precipitate is filtered and dried (20 g).

EXAMPLE 19

479 mg of Rhodamine B are suspended in 10 ml of pyridine and 802 mg of the potassium salt of bis(tridecafluorohexylsulfonyl)methane and 206 mg of dicyclohexylcarbodiimide are added. After stirring for 48 h, the mixture is filtered to remove the dicyclohexylurea and evaporated. The zwitterion obtained:

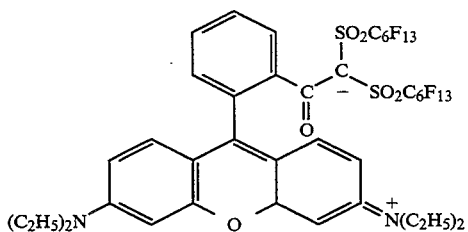

has intense coloring properties. It is soluble in polar polymers and makes it possible to form dye lasers.

EXAMPLE 20

Pyrrole-3-acetic acid (M=122) is prepared according to the method of D. Delabouglise (Thesis, Université de Paris-Nord, February 1991, "Contrôle Moléculaire des propriétés des polyméres" [Molecular Control of polymer properties]). 488 mg of this compound are dissolved in a mixture of 5 ml of acetonitrile and 1 ml of pyridine. 1,272 g of the potassium salt of bis(trifluoromethanesulfonyl)methane and 1.1 g of dicyclohexylcarbodiimide are added to the homogeneous solution. The mixture is stirred for 48 h at ordinary temperature and then the dicyclohexylurea precipitate is removed by centrifuging. The solvent is evaporated and the salt is purified by recrystallization from a butanone/1,2-dichloroethane mixture.

10 ml of a $5 \times 10^{-2}$M solution of the salt in acetonitrile is prepared and an electropolymerization is carried out in the anode compartment of an electrochemical cell on a platinum electrode. There is obtained a flexible conductive film of:

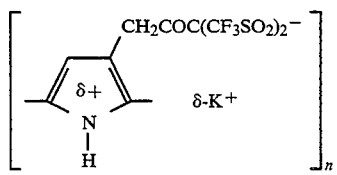

the doping (oxidation) of which is provided by exchange of cations and electrons with the outside. The conductivity of this material is of the order of 10 $(\Omega \cdot cm)^{-1}$ and is stable to the surrounding atmosphere. The electropolymerization carried out in the presence of unsubstituted pyrrole or pyrrole possessing oxyethylene linkages in the N or 3 position gives equally stable copolymers, the change in color of which can be used in forming electrochromic systems.

EXAMPLE 21

137 mg of p-aminobenzoic-acid (PABA) are treated with 250 μl of di-tert-butyl dicarbonate in pyridine. The solvent is evaporated and the t-BOC-PABA residue is suspended in 4 ml of acetonitrile and 1 ml of pyridine. 302 mg of the sodium salt of bis(trifluoromethanesulfonyl)methane and 165 mg of 1,1'-carbonyldiimidazole are added to this suspension. The mixture is stirred for 48 h and the excess reactant is removed using 10 μl of water. The solvent is removed using a rotary evaporator. The t-BOC protective group is removed by addition of 5 ml of a 0.2M solution of HBr in dioxane. The resulting suspension is filtered and the zwitterion:

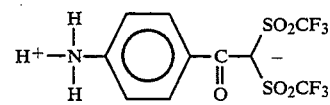

is purified by recrystallization from water. This compound forms complexes with polyethers: a network is formed by polycondensation of polyoxyethylene triol, with a mass of 2700, and of hexamethylenediisocyanate. Crosslinking is carried out by mixing the reactants in 50% solution in dichloromethane with a dibutyltin dilaurate catalyst. The homogeneous solution is pressed between two flat glass plates kept 300 μm apart by struts. Polycondensation is complete at ordinary temperature in 72 h. The resulting film is purified by extracting in a Soxhlet-type apparatus with acetone. The polymer/zwitterion complex is then formed by impregnating a disk ($\phi=1$ cm) of the polymer with 80 mg of the salt in solution in acetonitrile. This complex has a significant Kerr effect due to the orientation of the molecules of the zwitterion under the effect of an electric field.

EXAMPLE 22

The potassium salt of bis(pentafluorobenzenesulfonyl)methane was prepared by reacting pentafluorobenzenesulfonyl chloride with aluminum carbide in the presence of anhydrous potassium fluoride in acetonitrile. 260 mg of N,N'-disuccinimidyle carbonate [(SCO)$_2$CO] and 1 ml of pyridine are added to 212 mg of pentafluorobenzoic acid in suspension in THF. After the end of the reaction followed by the evolution of carbon dioxide, a homogeneous solution is obtained. 515 mg of the potassium salt of bis(pentafluorobenzenesulfonyl)methane are added to this solution of the activated ester. After reaction (complete in 1 h at 27° C.), the solvent is evaporated and the salt K$^+$[(C$_6$F$_5$SO$_2$)$_2$CCOC$_6$F$_5$]$^-$, insoluble in water, is separated by washing the hydroxysuccinimide formed during the reaction. The compound prepared can be used as a doping anion for electronic conductive polymers, of the polypyrrole or polyaniline type, on which it confers a stability with respect to the action of water and of oxygen. Moreover, this salt reacts with nucleophilic compounds by substitution of the fluorine atoms in the position para to the sulfonyl group. In particular, by reacting with polyamines containing at least two nitrogenous groups, it is possible to prepare polymers having ion exchange functions, which can be used, for example, for making fuel cell membranes.

Examples 23 to 30 illustrate applications of various compounds of the invention.

EXAMPLE 23

6.6 g of an ethylene oxide copolymer containing double bonds >C=C< and having a mass $M_w = 2.5 \times 10^5$ are dissolved in acetonitrile. 1.77 g of the salt of Example 17 and 165 mg of the radical initiator prepared according to Example 16 are added thereto. The solution is evaporated in a flat-bottomed PTFE cupel and the receptacle is placed in an oven under primary vacuum at 80° C. for 12 h. There is obtained a crosslinked elastomer in which the group —COC(SO$_2$CF$_3$)$_2$Li is fixed, arising either from the monomer or from the initiator. This material has a conduction by the lithium ions of $1.2 \times 10^{-5}$ (Ω·cm)$^{-1}$ at 26° C.

EXAMPLE 24

531 mg of the salt of Example 17 are dissolved in 5 ml of THF to which are added: 1 ml of the diallyl ether of poly(ethylene glycol) 400, 5 mg of chloroplatinic acid and 1.2 ml of triethoxysilane. The mixture is maintained at 60° C. until the bands characteristic of the Si-H bond at 2250 cm$^{-1}$ have disappeared. The mixture is filtered and the filtrate is added to 19.5 ml of methanol and 500 µl of water. A glass plate pickled in nitric acid and dried at 100° C. is steeped in the solution for 4 min. After rinsing with methanol and drying, the conductivity of the surface is $4 \times 10^{-5}$ Ω(squared).

EXAMPLE 25

100 g of an acrylonitrile (30%)-butadiene (70%) copolymer and 8 g of the salt of Example 18 are dissolved in acetone and the solvent is evaporated. The gummy mass is heated at 150° C. in a metal mold for 20 min. After cooling and removing from the mold, there is obtained a crosslinked polymer with good mechanical strength and having good antistatic properties, expressed by a conductivity of $10^{-8}$ (Ω·cm)$^{-1}$ at ordinary temperature.

EXAMPLE 26

1 g of the salt of Example 10 and 1.4 g of poly(ethylene oxide) with a mass $M_w$ of $5 \times 10^6$ are dissolved with magnetic stirring in 100 ml of methyl formate. The viscous solution is spread over a PTFE plate. By evaporation of the solvent, there is obtained an elastic film with a thickness of 120 µm and an ionic conductivity of $9 \times 10^{-5}$ (Ω·cm)$^{-1}$ at 300 K.

EXAMPLE 27

An electrochemical generator consists of a negative lithium electrode with a thickness of 45 µm deposited on an 8 µm polypropylene sheet, metallized with 100 nm of nickel. The electrolyte is prepared from the polyethylene glycol 400-cooxymethylene complex of mass $M_w \cong 10^5$ daltons prepared according to the method described in: C. V. Nicholas, D. J. Wilson, C. Booth & R. J. M. Giles, Brit. Polym. J., 20, 289 (1988), and from the lithium salt of trifluoromethanesulfonimide Li[(CF$_3$SO$_2$)$_2$N]. The concentration of the salt is calculated in order to correspond to one lithium cation per 25 oxygen atoms of the polyether, and the material is prepared in the form of a film with a thickness of 75 µm. The positive electrode is a composite material containing 45% by volume of lithium manganite of spinel structure LiMn$_2$O$_4$, milled to a particle size of $\cong$8 µm, 5% v/v of acetylene black and 50% v/v of an ionic conductor. The latter material is formed from the polyether constituting the electrolyte and mixed with 35% by weight of the salt of Example 11. The surface-active properties of the salt are used to advantage to produce a homogeneous dispersion of the constituents of the positive electrode in acetonitrile, making it possible, by a spreading technique, to produce films with a thickness of 80 µm on a current collector similar to that of the negative electrode. The device is obtained by laminating components to produce a flexible generator with a thickness of 210 µm. The e.m.f. is 3 V and the output is 500 mA/cm$^2$ at 30° C. for a voltage of 2.8 V. This system is rechargeable.

EXAMPLE 28

A secondary lithium generator is prepared in a way similar to Example 27, but replacing 10 mol % of the salt Li[(CF$_3$SO$_2$)$_2$N] of the electrolyte by the salt of Example 14: Li$_2${Fe[C$_5$H$_4$CO(CF$_3$SO$_2$)$_2$]$_2$}, so as to preserve the same O/Li ratio. This generator is then protected from overloading: for an external applied potential greater than 3.8 V, the ferrocene nucleus of the salt is oxidized to ferricinium. The corresponding species migrates to the negative electrode where it gives back the initial compound. This mechanism translates into a leakage current from the generator above the threshold potential of 3.8 V, preventing degradation of the system and having the advantage of not inducing self-discharge of the generator in an open circuit. This device is particularly advantageous for generators consisting of unit cells connected in series and whose capacitances are not exactly identical.

EXAMPLE 29

390 mg of the salt K[CH$_3$OCH$_2$COC(SO$_2$CF$_3$)$_2$] obtained in Example 7 are dissolved in 5 ml of dried acetonitrile to which 15 mg of anhydrous magnesium chloride have been added. The mixture is stirred for 4 h and the potassium chloride precipitate is removed by centrifuging. 800 mg of statistical ethylene oxide (80%)—methyl glycidyl ether (20%) copolymer with a mass $M_w \cong 2.5 \times 10^5$ are added to the supernatant solution. By spreading and evaporation of the viscous solution, there is obtained a polymer electrolyte film containing the magnesium in the form of the $\{Mg[CH_3OCH_2COC(SO_2CF_3)_2]_3\}^-$ complex The constitution of a primary generator is as follows:

| Mg | polymer electrolyte having an anionic vehicular mechanism transporting Mg ions | composite: graphite fluoride/ electrolyte/ acetylene black |
|----|----|----|

The electrolyte is that described in this example. The composition of the positive electrode corresponds to 42% v/v of the same electrolyte, 8% v/v of acetylene black and 50% v/v of graphite fluoride $CF_x$ ($x \cong 1$). The composite material diluted in acetonitrile is spread over a polypropylene sheet with a thickness of 8 μm metallized with 200 nm of copper, so as to form a layer with a thickness of approximately 80 μm. The negative electrode is a 20 μm sheet. The voltage of the battery after assembling the components by laminating at 80° C. is 2.5 V and the capacitance for an output of 400 μA/cm² is 7 mAh/cm².

EXAMPLE 30

426 mg of the monomer of Example 20 are dissolved in 5 ml of dried THF to which 42 mg of anhydrous lithium chloride are added. The KCl precipitate is removed by centrifuging and the remaining traces of potassium ions are exchanged by stirring with 1 g of Nafion ® resin in the Li+ form. The substituted pyrrole salt $(C_4H_3NH)CH_2COC(CF_3SO_2)_2Li$ is obtained by evaporating the THF. 5 g of vanadium pentaoxide $V_2O_5$ are added to 200 mg of this salt in acetonitrile and the suspension is stirred for 48 hours. A polypyrrole deposit forms at the surface of the oxide grains, the reaction translating into a color change from orange to green-black. The particles are separated by filtration; the oxide now has a surface electronic conductivity induced by the deposit of conductive polymer.

An electrochemical generator is constructed in a way similar to that of Example 27, replacing $LiMn_2O_4$ by an equivalent volume of treated vanadium oxide. The generator thus constituted has an open-circuit voltage of 3.2 V and now has a safety device which prevents overloading: below a potential of 2.7 V, the polypyrrole undergoes a redox reaction leading to its dedoping and a reduction in its conductivity of 5 orders of magnitude. The $V_2O_5$ grains are then insulated and lose their electroactivity. In a variant, the current collector of the positive electrode of the generator of Example 28 is covered with an $\cong 1$ μm film of modified polypyrrole, deposited by electropolymerization from an aqueous solution of the lithium salt. The generator thus assembled is also protected against overloading, an insulating polypyrrole layer being interposed between the current collector and the positive electrode for a potential of less than 2.7 V.

We claim:

1. A process for the preparation of a compound of the formula

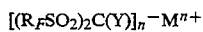

wherein Y is —C≡N or RZ— where Z is carbonyl, sulfonyl or phosphoryl and R is a monovalent organic radical;

M is a metal or an organic radical;

n is the valency of M; and $R_F$ is perfluoroalkyl or perfluoroaryl, comprising:

i) reacting a compound

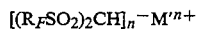

wherein $M'^{n+}$ is a metal or an organic radical, with a compound YX, where X is a halogen or a pseudohalide when Y is RZ—, and X is a halogen when Y is —CN;

in the presence of a nucleophilic aprotic base.

2. The process of claim 1, wherein said pseudohalide is selected from the group consisting of $RSO_3^-$, $RCO_2^-$, succinimidyloxy, phthalimidoxy, 1-benzotriazoloxy, oxynorbornene-2,3-dicarboximide, trifluoroethoxy, trichloroethoxy, imidazolyl, triazolyl, nitrophenoxy, dinitrophenoxy, perhalophenoxy and O-acylurea.

3. The process of claim 1, wherein said aprotic nucleophilic base is selected from the group consisting of trialkylamines, pyridines, imidazoles, amidines, guanidines and mixtures thereof.

4. The process of claim 1, wherein said aprotic nucleophilic base is selected from the group consisting of triethylamine, diisopropylethylamine, quinuclidine, 1,4-diazabicyclo[2.2.2]octane, pyridine, alkylpyridine, dialkylaminopyridine, N-alkylimidazole, imidazo[1,2-a]pyridine; 1,5-diazabicyclo[4.3.0]non-5-ene, 1,8-diazabicyclo[5.4.0]undec-7-ene, tetramethylquanidine, 1,3,4,7,8-hexahydro-1-methyl-2H-pyrimido[1,2-a]pyrimidine and mixtures thereof.

5. The process of claim 1, wherein said nucleophilic base is immobilized.

6. The process of claim 1, wherein said compound XY is a halide prepared in situ from an acid compound RZOH or a compound RZOM where M is a metal or an organic radical by reacting with a halogenating agent selected from the group consisting of $SOCl_2$, $SOBr_2$, $SF_4$, $(C_2H_5)_2NSF_3$, $COCl_2$ $(COCl)_2$, $(COBr)_2$, $(CCl_3O)_2CO$, $[(CH_3)_2N=CHCl]^+Cl$, triphenylphosphine/$CCl_4$ mixture, dichloromethyl methyl ether and mixtures thereof.

7. The process of claim 1 or 2, wherein when Y is RZ and Z is a carbonyl, then RZX is an anhydride RCO—O—COR.

8. The process of claim 7, wherein said anhydride RCO—O—COR is obtained in situ by reacting an acid RCOOH with a molecular dehydrating agent selected from the group consisting of carbodiimides, alkyl ethynyl ethers, succinimidyl carbonates, succinimidyl oxalates, $(SCO)_2C_2O_2)$, phthalimidyl carbonates, phthalimidyl oxalates, 1-benzotriazoyl carbonates, 1-benzotriazolyl oxalates, phthalimidyl carbonates, phthalimidyl oxalates, 1-benzotriazolyl carbonates, 1-benzotriazolyl oxalates, nitrophenyl oxylate, dinitrophenyl oxylate, perhalophenyl oxalate, nitrophenyl carbonate, dinitrophenyl carbonate, perhalophenyl oxylate, trifluoroethyl carbonate, trifluoroethyl oxalate, trichloroethyl carbonate, trichloroethyl oxalate, P$\phi_3$/diethylazodicarboxylate, P$\phi_3$/dithiodipyridine, carbonyldiimidazole, phenylphosphorodiimidazole, amide acetals, 2-alkoxy-1-alkoxycarbonyl-1,2-dihydroquinoline, O-benzotriazol-1-yl-N,N,N',N'-tetramethyluronium or O-benzotriazol-1-yl-N,N,N',N'-tetramethyluronium or O-benzotriazol-1-yloxytrisdimethylaminophosphonium salts, aromatic sultones, isobutyl chloroformate, diphenylphosphorchloroiridate, ethylene chlorophosphite, diethylethlene pyrophosphite, bis(2-oxo-3-oxazolidinyl)phosphinyl chloride and mixtures thereof.

9. The process of claim 1, wherein said salt of the cation M is selected from the group consisting of carbonate, phosphate, chloride and hydroxide of the cation M.

10. A compound of the formula $$[(R_FSO_2)_2C(Y)]_n^- M^{n+}$$

wherein Y is —C≡N or RZ— where Z is carbonyl or phosphoryl and R is a monovalent organic radical;
M is a metal;
n is the valency of M; and
$R_F$ is perfluoroalkyl or perfluoroaryl.

11. A compound of the formula $$[(R_FSO_2)_2C(Y)]_n^- M^{n+}$$

wherein Y is —C≡N or RZ— where Z is carbonyl, sulfonyl or phosphoryl and R is a monovalent organic radical;
M is an organic radical;
n is the valency of M; and
$R_F$ is perfluoroalkyl or perfluoroaryl.

12. A compound of the formula $$[(R_FSO_2)_2C(Y)]_n^- M^{n+}$$

wherein Y is —C≡N or RZ— where Z is carbonyl, sulfonyl or phosphoryl and R is a monovalent organic radical having more than 4 carbon atoms;
M is an alkaline-earth metal or a transition metal;
n is the valency of M; and
$R_F$ is perfluoroalkyl or perfluoroaryl.

13. The compound of any one of claims 10 to 12, wherein $R_F$ is $C_{1-20}$ perfluoroalkyl or $C_{6-20}$ perfluoroaryl.

14. The compound of any one of claims 10 to 12, wherein R is selected from the group consisting of $C_{1-30}$ alkyl, $C_{1-8}$ perhaloalkyl, $C_{6-12}$ aryl, $C_{6-12}$ perhaloaryl, arylalkyl, oxaalkyl, azaalkyl and thioalkyl.

15. The compound of any one of claims 10 to 12, wherein R contains contains an element selected from the group consisting of —C≡C—, —C≡C—C≡O, —C≡SO_2, —C≡Cφ, —OH, —NH_2, —COOH, —N≡C≡O, —O—O—, —N≡N, N_2≡CH—, —SO_2N_3 and —S—S—.

16. The compound of any one of claims 10 to 12, wherein R is mesomorphic or chromophoric.

17. The compound of any one of claims 10 to 12, wherein R contains an element selected from the group consisting of a hindered phenol, a quinone an amide, a nitrile, a disulfide, a thioamide, a ferrocene, a phenothiazine, a bis(dialkylaminoaryl) group, a nitroxide or an aromatic imide.

18. The compound of any one of claims 10 to 12, wherein RZ is a polypeptide or amino acid.

19. An ion conductive material comprising at least one salt, wherein said salt is a compound according to any one of claims 10 to 12.

20. The process of claim 1, wherein the solubility of a compound $M'_{1/n}X$ formed in the reaction medium is lower than that of a compound $(NuH)^+[(R_FSO_2)_2CY]^-$, wherein said process comprises
i) reacting a compound $$[(R_FSO_2)_2CH]_n^- M'^{n+}$$

wherein $M'^{n+}$ is a metal or an organic radical, with a compound YX,
where X is a halogen or a pseudohalide when Y is RZ—, and X is a halogen when Y is —CN;
in the presence of a nucleophilic aprotic base; and
ii) reacting the product of step i) with a salt of the cation M.

21. An ion conductive material comprising at least one salt, wherein said salt is a compound according to any one of claims 10 to 12; and
a solvent for said salt.

22. The ion conductive material of claim 21 wherein said solvent is selected from the group consisting of ethylene oxide copolymer, dialkyl ether of poly(ethylene glycol), acrylonitrile-butadiene, poly(ethylene oxide), polyethylene glycol-co oxymethylene, ethylene oxide-methylglycidyl ether copolymer and mixtures thereof.

* * * * *